United States Patent [19]
Schmid

[11] Patent Number: 5,425,917
[45] Date of Patent: Jun. 20, 1995

[54] APPARATUS FOR ATTACHING A LABELED PROBE AND/OR ANTIBODY TO MACROMOLECULES

[76] Inventor: Peter Schmid, 10431 Regent St., Los Angeles, Calif. 90034

[21] Appl. No.: 242,148

[22] Filed: May 13, 1994

Related U.S. Application Data

[63] Continuation of Ser. No. 973,840, Nov. 9, 1992, abandoned.

[51] Int. Cl.⁶ .................. G01N 33/00; G01N 27/28
[52] U.S. Cl. ............................ 422/63; 422/58;
422/81; 422/99; 422/110; 422/111; 422/116;
435/289; 366/208
[58] Field of Search .............. 422/63, 81, 99, 110, 422/111, 116, 58; 435/289; 366/208, 209, 333

[56] References Cited

U.S. PATENT DOCUMENTS

| | | | |
|---|---|---|---|
| 2,499,162 | 2/1950 | Rand | 366/208 |
| 3,036,894 | 5/1962 | Forestieve | 422/66 X |
| 3,154,294 | 10/1964 | Bittner | 366/208 |
| 3,224,737 | 12/1965 | Becker | 366/208 |
| 3,998,434 | 12/1976 | Gaynor | 259/73 |
| 4,125,335 | 11/1978 | Blume et al. | 366/209 |
| 4,307,965 | 12/1981 | Catarious et al. | 366/208 |
| 4,598,049 | 7/1986 | Zelinka et al. | 422/116 X |
| 4,702,610 | 10/1987 | Reynolds | 366/213 |
| 4,704,256 | 11/1987 | Hood et al. | 422/68 |
| 4,708,931 | 11/1987 | Christian | 435/7 |
| 4,726,889 | 2/1988 | Love et al. | 204/182.8 |
| 4,911,816 | 3/1990 | Love et al. | 204/299 R |
| 5,089,233 | 2/1992 | DeVaney et al. | 422/99 |
| 5,154,888 | 10/1992 | Zander et al. | 422/58 |

FOREIGN PATENT DOCUMENTS 0381501 1/1990 European Pat. Off. .

OTHER PUBLICATIONS

Sure Blot Hybridization Kit by Oncor (Selected Pages).
Sure Blot Product Information by Oncor (Two Pages).
Technical Update Genius Nonradioactive DNA Labeling and Detection Kit–Boehringer Mannheim Biochemicals.

*Primary Examiner*—James C. Housel
*Assistant Examiner*—Harold Y. Pyon
*Attorney, Agent, or Firm*—Harold L. Jackson

[57] ABSTRACT

An apparatus and method for attaching a labeled probe to macromolecules such as DNA/RNA fragments or proteins attached to a membrane utilizes a flexible bag having an inlet and an outlet port. Reagents including the probe to which the membrane is to be exposed during the labeling process are stored in reservoirs. Pumps are provided to selectively transfer reagents from reservoirs to the inlet port and for selectively evacuating the bag via the outlet port so that reagents from the individual reservoirs can be sequentially supplied to or removed from the bag while the membrane is positioned therein. One or more rollers are arranged to roll back and forth over the top of the bag to uniformly expose the membrane to the reagent within the bag.

24 Claims, 4 Drawing Sheets

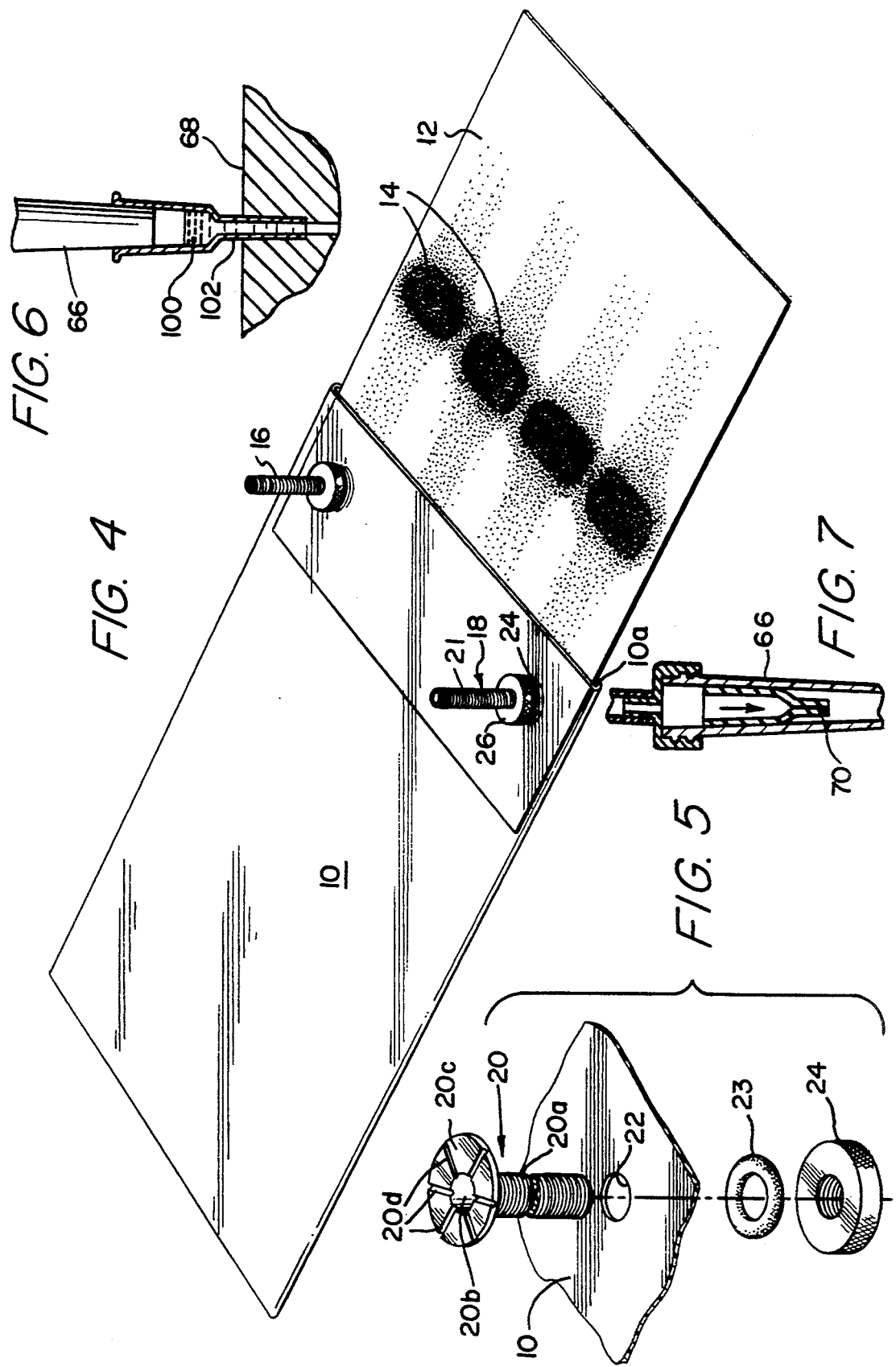

APPARATUS FOR ATTACHING A LABELED PROBE AND/OR ANTIBODY TO MACROMOLECULES

This is a continuation of application Ser. No. 07/973,840, filed Nov. 9, 1992, now abandoned.

BACKGROUND OF THE INVENTION

1. Field of the Invention

The present invention relates to an automated apparatus and method for attaching a labeled probe and/or an antibody to macromolecules such as nucleic acid fragments and proteins.

2. Description of the Prior Art

The detection of certain macromolecules such as nucleic acid ("DNA/RNA") strands or proteins of interest which have been physically separated from other macromolecules on a molecular weight basis, for example, by electrophoresis and transferred to a filter or membrane has generally been accomplished manually. Typically the membrane carrying the separated macromolecules is inserted in a plastic bag (or box).

A plurality of reagents are sequentially added to and removed from the bag with the bag being sealed after each reagent is added so that the reagent can be agitated, for example, by shaking the bag to uniformly dispose the membrane to the reagent. The bag then must be unsealed when one reagent is to be removed and a new one added.

As an example, the Biochemicals Division of Boehringer Mannhein of Indianapolis, Ind. ("Boehringer") suggests the following procedure for hybridizing labeled (non-radioactive) DNA to immobilized target DNA affixed to a nitrocellulos filter or nylon membrane. The filter or membrane is initially prehybridized by sealing each filter in a plastic bag (or box) with a quantity (e.g. 20 ml/100 cm² of filter) of hybridization solution for about one hour. The solution is redistributed over the filter periodically by manually moving or shaking the bag.

The bag is then opened and the prehybridization solution removed and replaced with an additional quantity of hybridization solution containing a small quantity (e.g., 25 ng) of labeled and freshly denatured DNA. Care must be taken to prevent the filters from becoming dry when exchanging the solutions.

The bag is then resealed and the filter incubated at an appropriate temperature for several hours. To ensure the exposure of the filter to the labeled DNA and hybridization solution during the incubation period, the bag should be shaken or otherwise agitated from time to time.

The bag is them reopened, the excess labeled DNA and solution removed. A wash solution is then inserted into the bag, the bag sealed and agitated to further remove unattached labeled DNA and hybridization solution from the bag. Additional washing steps may be used.

An antibody conjugate solution replaces the wash solution and the filter is incubated for an appropriate time to allow the antibody to bind to the labeled DNA. The unbound antibody is removed and the filter washed. The bag is also agitated during these additional steps. The filter is then exposed to a prepared color developer which reacts with the antibody to produce a colored precipitate identifying the target DNA.

The use of a radioactive substance to form the labeled DNA eliminates the antibody and color forming steps. The location of the radioactive material may be detected by photographic techniques. However, the precautions required in handling radioactive material may more than offset the antibody and color developer steps.

The identity of target proteins separated by, for example, the Western Blotting technique requires steps similar to the steps outlined above with respect to hybridizing labeled non-radioactive DNA to target DNA except that the labeled probe consists of an antibody which contains a phosphorescent material or has an enzyme attached to it which will allow for either a color substrate development or a chemiluminescent development, as is well known to those skilled in the art.

All such macromolecule identification techniques require that the filter or membrane be exposed sequentially to several reagents. The manual operation required to fill, seal, open, drain and refill the bag for each step is time consuming and costly. In addition one or more of the reagents such as the labeled probe (DNA/RNA strand or proteins) and the antibody conjugate (for non-radioactive DNA/RNA detection) are very expensive. To conserve costs it is desirable to use very small quantities of such reagents. However, the ability to ensure that the filter is uniformly exposed to the reagents during the incubation step by manually agitating or shaking the bag is not compatible with a very small volume of solution.

There is a need for a more efficient and less costly system for identifying macromolecules of interest which have been separated from other macromolecules and bound to a filter or membrane.

SUMMARY OF THE INVENTION

In accordance with my invention an apparatus for attaching a labeled probe to macromolecules such as DNA/RNA fragments or proteins attached to a membrane includes a plurality of liquid reservoirs. Each reservoir contains a solution to which the membrane or filter is to be exposed during the labeling process with one reservoir containing the probe. A flexible bag is provided for receiving the membrane and includes an inlet and an outlet port through which liquid may be inserted into and removed from the bag while the membrane is disposed within the bag. Means such as pumps are provided to selectively transfer liquid from the reservoir to the inlet port of the bag and for selectively evacuating the bag so that reagents from the individual reservoirs can be sequentially supplied to and removed from the bag.

Preferably means such as a tiltable tray or cage on a thermal controlled table is provided for supporting and periodically tilting the bag about a horizontal axis to cause liquid within the bag to flow back and forth across the surface of the membrane. In addition, one or more rollers may be disposed within the tray to roll back and forth over the top surface of the bag during the tilting action to uniformly expose the membrane to very small quantities of solution within the bag.

The features of the invention may best be understood by reference to the following description taken in conjunction with the accompanying drawings.

BRIEF DESCRIPTION OF THE DRAWINGS

FIG. 4 is a perspective view of one of the bags of FIG. 1 with a developed membrane extending through an open end of the bag;

FIG. 5 is an exploded perspective view of one of the inlet/outlet ports incorporated into the bags of FIG. 1;

FIG. 6 is a cross-sectional view of one of the metering pipette tips for holding the antibody and a portion of the manifold of FIG. 1; and FIG. 7 is a cross-sectional view of a backflow prevention valve affixed to the inlet end of the pipettes used in the apparatus of FIG. 1.

DESCRIPTION OF THE PREFERRED EMBODIMENT

Figure 1:
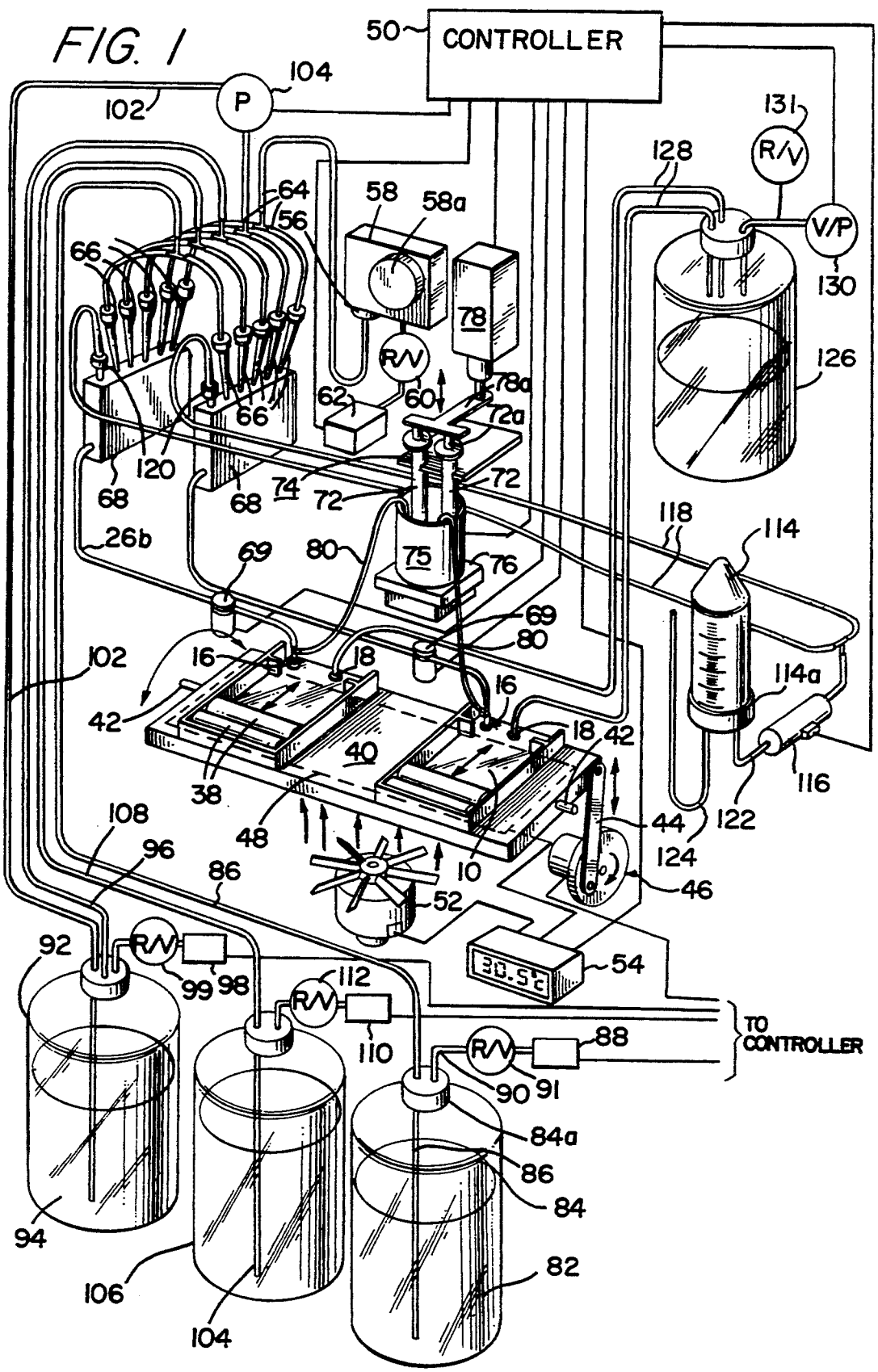
FIG. 1 is a schematic drawing of an apparatus in accordance with the invention particularly adapted for the non-radioactive labeling of DNA/RNA strands.
Figure 3:
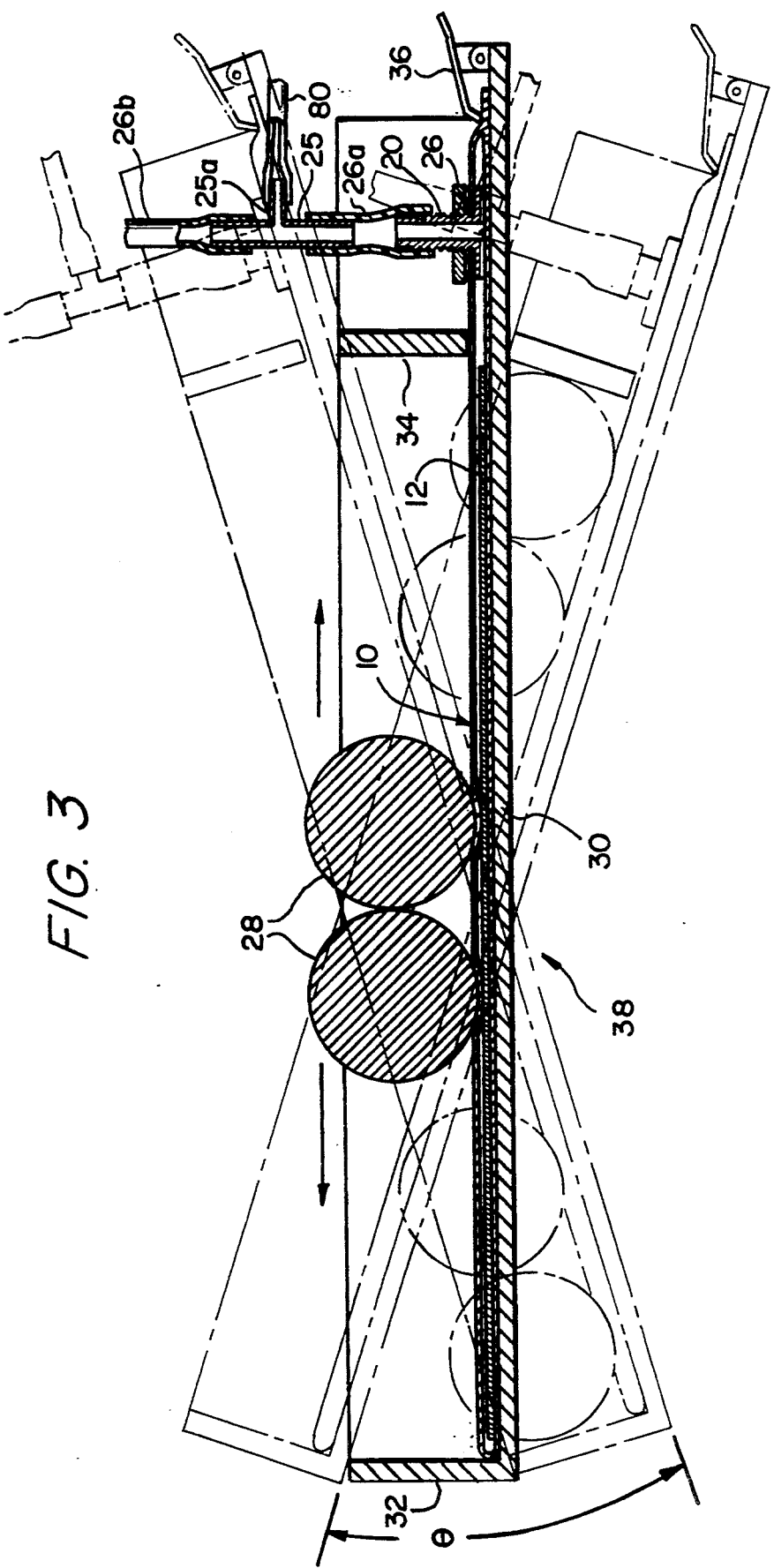
FIG. 3 is a cross-sectional view of one of the bags, the tiltable tray and the rollers shown in FIG. 1.

Referring now to the drawings and more particularly to FIGS. 1, 3, and 4 a pair of thin flexible bags 10, made for example of polyethylene or other suitable plastic, are provided for receiving the membranes or filter 12 to which macromolecules such as DNA/RNA strands or proteins of interest (designated at 14) have been attached. The macromolecules may be separated on a molecular weight basis by one of the accepted techniques, such as the Southern Blot, Western Blot, etc., known to those skilled in the art and transferred to the membranes 12 by a vacuum or other well known technique. See, for example, U.S. Pat. No. 4,911,816. The macromolecules 14 as transferred to the membrane would not be visible and hence the need to attach a label thereto which can be identified visually.

The bags 10 include an inlet port 16 and an outlet port 18. Each such port is formed by a hollow nipple 20 having a threaded stem 20a which extends through an opening 22 in the bag, a sealing gasket or O ring 23 and a threaded nut 24 as is best illustrated in FIGS. 4 and 5. The nipple includes a central passageway 20b and flat head (or lower surface) 20c with radial grooves 20d therein. The nipple head 20c is positioned in the interior of the bag 10. With the bag in its normally collapsed or flat condition, liquid may enter or exit the bag through the nipple 20 via grooves 20d and the central passageway 20b. The bags 10 are approximately the size of the membrane and include a large sealable opening 10a through which the membrane is inserted as is illustrated in FIG. 4. The openings 10a are sealed (e.g., by a heat sealing technique) once a membrane is inserted therein so that the inlet and outlet ports provide the only access to the interior of the bags. A T-fitting 25 is connected between the stem 20a of each inlet port and a reagent distribution manifold (to be described) by means of tubing 26a and 26b. The side inlet 25a of the T-fitting is provided for receiving the labeled probe as will be described.

Referring again to FIG. 1 and also to FIG. 3, the bags 10, when sealed with the membrane inside, are positioned in trays 28. Each tray has a flat bottom 30, which serves as a support surface for the respective bag 10, a U-shaped upstanding side wall 32 and a pair of inwardly projecting stub walls 34. The stub walls have a bottom surface which extends above the tray bottom 30 to accommodate the sides of the bag 10 with the inlet and outlet ports positioned forward of the walls 34 as is illustrated in FIG. 3.

A pair of spring biased clips 36 (only one of which is shown) are mounted on the tray bottoms 30 for releasably holding the forward end of a bag 10 on the tray. The bags 10 are of any suitable size to accommodate the membranes in use. Typically the bags will be about 10×12 cm.

A pair of rollers 38 (sometimes referred to as spreading members), made of nylon or other suitable low friction material, are positioned within each tray 28 and on the top surface of the associated bag 10 as is illustrated in FIGS. 1 and 3. The rollers roll back and forth over the top surface of the bags 10 as a result of a periodic tilting of the tray about a horizontal axis for continuously and uniformly distributing solution within the bags over the membranes. The rollers 38 rest on the top surface of the bags 10 and apply a substantially constant pressure on that surface by force of gravity. The rollers are free to move up or down relative to the bag support surfaces or tray bottoms 30 to accommodate different volumes of solutions within the bags. The distance of the rollers above the bag support surface 30 is self adjusting, that is, as the level of fill of the bag increases the distance increases and visa versa. The side walls 32 of the trays 28 prohibit lateral movements of the rollers and rotations of the roller axes.

Referring now to FIG. 1, the trays 28, which have a longitudinal axis parallel to the direction of movement of the rollers 38, are suitably secured on a table 40 which is mounted on a suitable support (now shown) for rotation about horizontal stub axles 42. A link 44 is pivotally mounted at one end to one corner of the table 38 and the other end to a motor driven tilt wheel 46. The motor driven wheel 46, under the control of a central controller or processor 50, oscillates the table through an appropriate angle $\Theta$ (FIG. 3) within the range of about 5° to 25° and preferably 15°. Heat is supplied to the table via an electric heater 48 embedded within or suitable affixed to the table. Current to the heater is supplied by a conventional power main (not shown) and controlled by the controller. Heat is removed from the table by an electric fan 52 which is also controlled by the controller 50. A display unit 54 provides a digital readout of the temperature of the table.

Reagents suitable for nonradioactive DNA labeling can be obtained in kit form. Such reagents include a prehybridization solution or blocking buffer to prevent non-specific binding of the labeled probe (to be described) to the membrane. The prehybridization solution may be prepared from the following constituents:

5×SSC; 0.1% (w/v) N-lauroylsarcosine, Na-salt (Sigma)

0.02 % (w/v) SDS

Add to the freshly prepared solution 1% (w/v) blocking reagent (vial 11 furnished by Boehringer).

The prehybridization solution (100 ml) is stored in a vial 56 disposed within an electric heater unit 58. The heater includes a manual control knob 58a for adjusting the temperature. The prehybridization vial 56 has an inlet connected through a pressure relief valve 60 to an electrically driven air pump 62 (under the control of controller 50). The prehybridization vial has an outlet connected through tubing 64, associated flow restrictor pipettes 66, solution distribution manifolds 68, tubing 26b and solenoid operated pinch valves 69 to the inlet ports 16 of the bags 10 as is illustrated in FIG. 1. The pinch valves 69 are normally closed i.e., pinching the flexible tubes 26b to a closed position. The controller 50 causes the pinch valves to open during the injection of a reagent into the bags 10. Each pipette 66 includes a duckbill type back flow valve 70 at the top thereof to prevent solution within the manifold from flowing back into the reagent containers. See FIG. 7.

Figure 2:
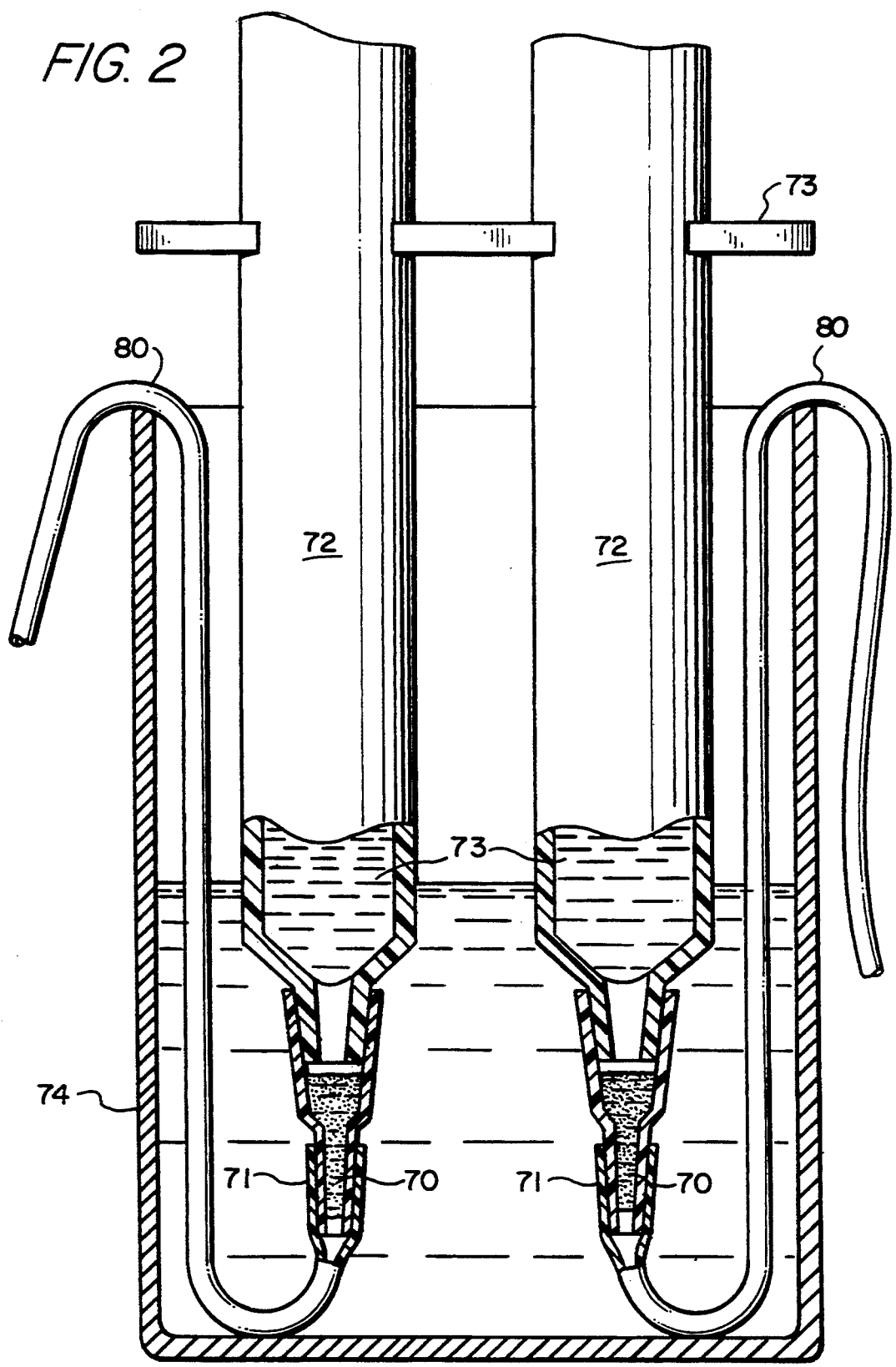
FIG. 2 is a side elevational view, partially in cross section, of the pair of syringes shown in FIG. 1 which hold the labeled probe.

A small quantity of nonradioactive digoxigenin labeled DNA probe 70 (e.g., 2 µg in 10 µl of solution) is contained in each of two pipette tips 71 secured to the discharge ends of syringes 72 (see FIG. 2). The probe may be prepared, for example, by a Nick translation, random priming or polymerase chain reaction procedure from a sample clone containing the sequence to be detected. The syringes 72 contain a small quantity (e.g. 3 ml) of hybridization solution 73 (same as the prehybridization solution discussed above) to minimize the dilution of the probe.

The syringes 72 are held in place by a bracket 74 so that the lower portions thereof including the pipette sections 71 are immersed in a water bath contained within a container 75. The water bath is positioned on a plate 76 and electrically heated via heater wires (not shown) embedded in the container 75. Current to the heater wires is controlled by the controller 50. A syringe pump 78 (under the control of the controller 50) is arranged to depress the syringe plungers 72a via a plate 78a to force the hybridization solution within the syringes and the labeled probe within the pipette sections 71 into the inlet ports of the bags 10 through tubing 80. See FIGS. 1 and 3. The use of tubes 80 and side inlets 25a of the T-sections 25 minimizes the quantity of labeled probe that is necessary and prevents probe contamination of the manifolds.

A quantity of buffer/wash 82 (comprising, for example, 0.3M NaCl; 0.03M Na-citrate; pH 8.0(20° C.)) is contained in a container or bottle 84. A cap 84a seals the top of the bottle. The buffer/wash solution is supplied to the inlet ports of the bag 10 through tube 86, associated pipettes 66, manifolds 68 and tubes 26b. An electrically driven air pump 88, under the control of controller 50, supplies air under pressure to the top of the bottle 84 via tube 90. The air pressure on the top of the liquid within bottle 84 forces the liquid through the tube 86 and into the inlet ports of the bag. The quantity of liquid delivered from the bottle depends upon the air pressure provided by the pump, the pumping time and the size of the metering ports in the associated pipettes 66. A pressure relief valve 91 is opened when the air pump is deactivated to reduce the pressure within the bottle to atmospheric in order to stop the flow immediately.

A buffer no. 1 solution 92 is contained within a bottle or container 94. Buffer no. 1 is supplied to the inlet ports of the bags through tubing 96, associated pipettes 66, manifolds 68 etc. Again the quantity of the solution within the bottle 94 delivered to the bags 10 is controlled by an electrically driven air pump 98. Another pressure relief valve 99 relieves the pressure on the top of the solution as soon as the pumping action is terminated. Buffer no. 1 may be prepared from 100 mM Tris-HCl; 150 mM NaCl; pH 7.5(20°).

Buffer no. 1 is alternatively delivered along with a antibody conjugate solution via tube 102, electrically driven positive displacement pump 104 (under the control of controller 50), associated pipettes 66, manifolds 68 and tubes 26b to the inlets of the bags. A small quantity (e.g. 8 µl) of the antibody conjugate 100 is stored in two metering sections 102 attached to the ends of the associated pipettes 66. The discharge ends of the metering sections 102 are disposed in openings in the manifold 68 as is illustrated in FIG. 6. The antibody conjugate is part of the DNA labeling kit provided by Boehringer.

A buffer no. 2 solution 104 contained within a bottle or container 106, is supplied to the inlet ports of the bags 10 through tubing 108 and associated pipettes 66 etc. Again an electrically driven air pump 110 supplies air to the top of the container 106 and pressure relief valve 112 relieves the pressure within the bottle as soon as the pumping action has ceased.

Buffer no. 2 pretreats the membrane after the antibody conjugate has attached to the labeled probe in advance of the addition of a coloring solution (not shown) for providing a colored label at the target DNA sites. The air pumps 88, 98 and 110 as well as the relief valves are operated by controller 50.

An antibody blocking buffer, supplied by Boehringer or another suitable source, is stored in a vial 114 and supplied to the inlet ports of the bags 10 by means of a positive displacement pump 116 (under the control of controller 50), tubes 112, and pipette tips 120. The antibody blocking buffer is transferred to the bags 10 in advance of the antibody to prevent non-specific binding of the antibody to the membrane. The vial 114 includes a cap 114a which has an outlet connected to the pump 116 via tube 122. A breather tube 124 allows air to enter the cap and vial to replace buffer transferred to the bags.

A waste container or bottle 126 is connected to the outlet ports 18 of the bags 10 via tubes 128 and also to a vacuum pump 130 (under the control of controller 50). A cap 126a seals the top of the container 126. When actuated the pump 130 provides a low or subatmospheric pressure within the container 126 and the tubes 128 to withdraw fluid (air and/or liquid) from the bags 10. A relief valve 131 restores atmospheric pressure within the container 126 when deactivated. A check valve (not shown) inside each of tubes 128 prevents any back flow to the bags 10.

The following protocol (DNA labeling) provides an example of the use of the apparatus and method with respect to labeling macromolecules separated by molecular weight, for example, and attached to a membrane or filter. Initially, the various vials, containers, pipette tips and syringes are filled with an appropriate supply of the chosen reagents as discussed above. A membrane or filter 12 with the separated DNA segments of interest attached thereto (e. g. by a conventional gel electrophoresis and membrane transfer technique) is placed in each of the bags 10. The bags are then sealed and the controller activated to process the membranes through the following steps:

PREHYBRIDIZING

1. All air is removed from the bags via vacuum pump 130, the tubes 128 and the outlet ports.

2. Air pump 62 is activated for a preset time to inject a prescribed quantity (e.g. 10 ml) of the prehybridization solution from vial 56 into the bags through the inlet ports thereof. The table 40 is heated by the electrical heating element to a temperature of about 68° C. The table is also oscillated by the motor driven tilt wheel 46 to cause the rollers 48 to roll back and forth across the top surface of the bags to continually mix and redistribute the solution over the membranes. The step duration is about one to one and a half hours. It should be noted that the table 40 is oscillated during each of the subsequent steps to ensure that membranes are thoroughly exposed to the reagents within the bags 10.

3. Just prior to the termination of step 2, (e.g., 10 minutes) heat is supplied to the beaker support plate 76 to bring the temperature of the waterbath in the beaker 78 to boiling or near boiling temperature. This step results in a denaturation of the labeled DNA probe (i.e., separating the strands thereof).

4. Vacuum pump 130 is energized to drain the prehybridization solution from the bags 10.

HYBRIDIZATION WITH PROBE

5. Solenoid 78 is energized to inject the labeled probe (e.g., 8 μl) along with the hybridization solution (e.g., 3 ml) in syringes 72 into the bags. The membranes are then incubated for four to six hours with the table temperature set at about 65°. The denatured labeled probe binds to the immobilized target DNA strands affixed to the membrane while the hybridization solution blocks the probe from binding to the membrane per se.

6. The contents of the bag are drained via the vacuum pump.

7. The table is cooled by means of fan 52 to about 55° C. The wash buffer 82 is then added to the bags and the membranes incubated for about twenty minutes.

8. The bags are drained, removing excess probe.

9. Wash buffer 82 is again added to the bags and the membranes incubated for about 20 minutes as in step 7.

10. The bags are drained.

11. Wash buffer is again added to the bags and the membranes left to incubate for about twenty minutes.

12. The bags are drained.

13. The table is cooled to about room temperature.

IMMUNOSTAINING

14. Buffer no. 1 is added (e.g., 10–15 ml) and the membranes are left to incubate for about two minutes.

15. The bags are drained.

16. Buffer no. 1 is again added and the membranes are left to incubate for about two minutes.

17. The bags are drained.

18. A prescribed quantity of antibody blocking buffer (e.g., 10–15 ml) is added to the bags via pump 116 and the membranes left to incubate for about thirty minutes.

19. The bags are drained.

20. Buffer no. 1 (e.g., 10–15 ml) is then added and the membranes are left to incubate for about two minutes.

21. The bags are drained.

22. Buffer no. 1 is added and the membranes are left to incubate for about two minutes.

23. The bags are drained.

24. The antibody conjugate solution 100 is injected along with buffer no. 1 via pump 104 and the membranes are left to incubate for about thirty minutes. The antibody binds to the DNA probe. The antibody includes an enzyme which is adapted to react with a developing solution to produce a colored precipitate as will be explained.

25. The bags are drained.

26. Buffer no. 1 is added and the membranes are left to incubate for about two minutes.

27. The bags are drained.

28. Buffer no. 1 is added and the membranes are left to incubate for about two minutes.

29. The bags are drained.

30. Buffer no. 1 is added and the membranes are left to incubate for about two minutes.

31. The bags are drained.

32. Buffer no. 1 is added and the membranes are left to incubate for about two minutes.

33. The bags are drained.

34. Buffer no. 1 is added and the membranes are left to incubate for about two minutes.

35. The bags are drained.

36. Buffer no. 3 (e.g., 10–15 ml) is added and the membranes are left to incubate for about two minutes.

37. The bags are drained.

38. Buffer no. 3 is added and the membranes are left to incubate for about two minutes.

39. The bags are drained.

40. Buffer no. 3 is added and the membranes are left to incubate for about two minutes.

41. The bags are drained.

42. End.

The above procedure attaches a labeled probe (including a color producing antibody) to the target DNA strands. The label can be detected or made visible by the addition of a suitable developer solution to the membranes within the bags and allowing the membranes to incubate in the dark for a few minutes. The resulting colored (e.g., dark brown) bands or marks 14 (FIG. 4) identifying the target DNA can be documented by conventional photographic or photocopying techniques. Boehringer provides an NBT solution and an x-phosphate solution which can be added to a Tris buffer in the following amounts to prepare the developer:

45 μl NBT + 35 μl + X-phosphate to 10 ml of 10 mM Tris - HCl; 1 mM EDTA at ph 8.0 (20° C.).

The apparatus and method described above may be used for radioactive DNA/RNA labeling by using a radioactive probe. In this case, the immunostraining steps and associated reagents are unnecessary.

The apparatus and method may also be used to stain proteins (deposited on a membrane via the Western Blot technique, for example) with a labeled probe in the form of an antibody. In this case, the target or template is a protein and not a nucleic acid. The use of blocking agents and buffers remains the same although the formulations thereof may differ. There is, of course, no need for the denaturation step and the number of reagents can be reduced. The antibody probe for attachment to the target protein may be detected either by fluorescent labeling by primary or secondary antibody or by attachment of an enzyme to the antibody which in turn allows final detection by a color substrate development or chemiluminescent development. Similarly DNA probe visualization can be achieved using fluorescent or chemiluminescent techniques well known in the art.

There has thus been described a novel apparatus and method for attaching a labeled probe to macromolecules (RNA/DNA or proteins) affixed to a membrane or filter. Various modifications both as to the apparatus and method will become apparent to those skilled in the art without involving any departure from the scope and spirit of my invention as set forth in the appended claims. For example, all of the reagents may be injected into the bags by means of positive displacement pumps such as pumps 104 or by using air pressure such as pumps 88, 99 and 112. The number of times that a wash or buffer solution is added to the bags is a matter of choice.

It should be noted that there are alternative mechanisms for causing a roller to move back and forth across the top surface of a bag containing liquid reagents to uniformly distribute the same over the top surface of a membrane within the bag. For example, the membrane could be uniformly exposed to very small quantities of reagents by securing the bag to a curved surface (e.g., cylindrical) which is oscillated around a horizontal axis. A roller can be mounted, for example, on a stationary axel positioned above and parallel to the curved surface so that the roller presses against the top surface of the bag (via gravitational force). With this type of arrangement, the roller will distribute the liquid reagent within the bag back and forth across the top surface of the membrane as the curved surface rotates back and forth around its horizontal axis. The curved surface may be in the form of a bottle filled with a thermally controlled liquid.

What is claimed is:

1. An apparatus for attaching a labeled probe to macromolecules affixed to a planar membrane by exposing the membrane in a series of sequential process steps to different solutions in which the volume of the solutions to which the membrane is exposed vary over a wide range comprising:
   a plurality of liquid reservoirs, each reservoir containing a solution to which the membrane is to be exposed during one or more of the labeling process steps, one of the reservoirs containing the labeled probe;
   a support surface;
   a flexible bag approximately the size of the membrane disposed on the support surface for receiving the membrane, the bag having a large sealable opening through which the membrane is inserted into the bag and an inlet and outlet port through which solution can be inserted into and removed from the bag, respectively;
   means for selectively supplying at least one quantity of solution from each of the reservoirs to the inlet port of the bag;
   a spreading and mixing member in contact with the surface of the bag opposite the support surface;
   spreading means for moving the spreading member back and forth over said bag surface to continuously distribute and spread the solution over the surface of the membrane, the spreading member being moveable toward and away from the support surface while maintaining a substantially constant pressure towards the top surface of the bag to accommodate the different volumes of solution within the bag whereby the membrane and the macromolecules affixed thereto can be continuously exposed to each portion of the solution during each process step notwithstanding the presence of widely different volumes of solution within the bag during the series of steps; and
   means connected to the outlet port of the bag for selectively evacuating the bag to allow another solution to be supplied to the then empty bag or to allow the membrane to be removed.

2. The apparatus of claim 1 wherein the flexible bag is formed of a heat sealable plastic.

3. The apparatus of claim 2 wherein the spreading member is in self adjusting contact with the top surface of the bag.

4. The apparatus of claim 3 wherein the reservoir containing the labeled probe includes heating means for selectively heating the solution containing the labeled probe to about 95 degrees centigrade.

5. The apparatus of claim 1 wherein the spreading member includes at least one roller positioned on top of the bag and means for moving the roller relative to the bag so that the roller moves back and forth across the top surface of the bag.

6. The apparatus of claim 5 further including a plurality of refillable liquid reservoirs, each reservoir containing one of the reagent solutions for use in at least one of the series of labeling process steps and at least three of the reservoirs containing sufficient reagent solution for use in multiple steps.

7. The apparatus of claim 5 wherein the at least one roller comprises two rollers.

8. The apparatus of claim 7 including means for selectively heating and cooling the bag to transfer heat into or from the solution in the bag.

9. The apparatus of claim 1 wherein the support surface is nominally positioned horizontally and wherein the spreading means includes means for periodically tilting the support surface relative to the horizontal to cause the spreading member to move back and forth across the surface of the bag without restricting its movements perpendicular to the plane of the bag to allow it to adapt to the changing shape of the top surface of the bag while maintaining a substantially constant pressure towards said surface.

10. The apparatus of claim 9 wherein the spreading means further includes a tray for holding the bag, the bottom of the tray forming the support surface and wherein the means for tilting the support surface tilts at least one end of the tray up and down with respect to a horizontal axis.

11. The apparatus of claim 10 wherein the tray has a longitudinal axis and includes upstanding sides along at least two edges parallel to the longitudinal axis and wherein the tilting means is arranged to tilt the tray around a horizontal axis perpendicular to the parallel sides and wherein the spreading member comprises at least one roller disposed within the tray and positioned on top of the bag, the roller being arranged to roll back and forth over the top surface of the bag in response to the periodic tilting of the tray, the roller having freedom of movement perpendicular to the plane of the bag to allow the roller to adapt to the changing shape of the top surface of the bag while maintaining a substantially constant pressure towards said top surface.

12. The apparatus of claim 11 wherein the tray tilting means comprise a table pivotally supported along said horizontal axis, and means coupled to one end of the table for oscillating the table through a total angle within the range of about 5 to 30 degrees.

13. The apparatus of claim 11 wherein each of the inlet and outlet ports comprise an opening in the top surface of the bag and a nipple within the opening, the nipple having a fluid passageway therethrough, a top portion extending outside of the bag and a headed portion positioned within the bag, the headed portion having a flat lower surface adapted to rest against the lower inside surface of the bag and at least one groove therein for conducting fluid between the bag interior and the passageway in the nipple.

14. The apparatus of claim 13 wherein at least one of the reservoirs is closed and includes an inlet opening and an outlet opening disposed below the liquid level and wherein the liquid supplying means for said at least one reservoir includes conduit means having a restricted orifice therein connected between the outlet opening in said reservoir and the passageway in the nipple, means for supplying air or gas under pressure to the inlet opening in said reservoir and timing means for controlling the pressurizing means to control the quantity of liquid transferred from said reservoir to the bag.

15. The apparatus of claim 14 including metering means for metering each quantity of liquid supplied to the inlet port of the bag from at least three reservoirs.

16. The apparatus of claim 15 further including means for heating at least that portion of the table which supports the tray.

17. The apparatus of claim 16 further including means for cooling at least that portion of the table which supports the tray to a predetermined temperature.

18. In an apparatus for attaching a labeled probe to macromolecules affixed to a substantially flat membrane by exposing the membrane when placed within a flexible bag to a series of different reagent solutions during sequential processing steps with the volumes of the solutions to which the membrane is exposed during the individual process steps varying over a wide range, the combination comprising:
   a substantially flat support surface nominally aligned horizontally for supporting the flexible bag so that a top surface of the bag extends above the support surface;
   at least one roller member having an axis of rotation parallel to the support surface, the roller member being in contact with the top surface of the bag;
   means for guiding the roller member so that lateral movements of the roller member and rotations of its axis are prohibited while permitting the roller member to freely move up or down with respect to the support surface while remaining in contact with the top surface of the bag as the configuration of the bag changes in response to different volumes of reagent solution therein; and
   means for causing the roller member to move back and forth across the top surface of the bag to continuously mix and distribute the solution across the membrane whereby the roller member remains in substantially constant pressure contact with the top surface of the bag as the configuration of the bag changes in response to different volumes of reagent solution therein.

19. The apparatus of claim 18 wherein the roller member moving means includes means for oscillating the support surface about a horizontal axis to cause the roller member to move back and forth across the top surface of the bag by force of gravity.

20. The apparatus of claim 18 further including a tray having at least two upstanding sides arranged parallel to the direction of movement of the roller member, the bottom of the tray defining the support surface, wherein oscillating means is arranged to tilt the support surface about a horizontal axis perpendicular to the direction of movement of the roller member within a angle between about 5° to 30°.

21. In an apparatus for attaching a labeled probe to macromolecules deposited on a substantially flat membrane by exposing the membrane in a series of sequential process steps to different reagent solutions of varying volumes, the combination comprising:
   a tray having a substantially flat bottom surface;
   means for positioning the tray so that the bottom surface is nominally positioned horizontally;
   a flexible heat sealable plastic bag for holding the membrane and the solutions, the bag being disposed within the tray and positioned on the bottom surface thereof;
   at least one roller member positioned within the tray and on top of the bag and free to move up or down relative to the support surface to accommodate different quantities of solution within the bag, the roller member arranged to apply pressure to the top of the bag by force of gravity, the roller member having a longitudinal axis; and
   means for causing the roller member to move back and forth across the top of the bag to uniformly distribute and continuously mix the solution across the membrane.

22. The apparatus of claim 21 wherein the last named means comprises means for periodically tilting the tray about a horizontal axis parallel to the longitudinal axis of the roller member so that the force of gravity causes the roller member to move across the top of the bag.

23. The apparatus of claim 22 further including a table for supporting the tray and means for selectively heating and cooling the tray to allow a proper binding action between the labeled probe and the macromolecule.

24. The apparatus of claim 23 wherein the table is rotatably supported along said horizontal axis and wherein the means for tilting the tray comprises means coupled to one end of the table for pivoting the table about said horizontal axis so that the tray is tilted up and down within a total angle of about 5 to 30 degrees.

* * * * *